US010729875B2

(12) United States Patent
Geerlings et al.

(10) Patent No.: US 10,729,875 B2
(45) Date of Patent: Aug. 4, 2020

(54) SYSTEM AND METHOD FOR ADJUSTING DURATION OF SENSORY STIMULATION DURING SLEEP TO ENHANCE SLOW WAVE ACTIVITY

(71) Applicant: KONINKLIJKE PHILIPS N.V., Eindhoven (NL)

(72) Inventors: Alexander Cornelis Geerlings, Boxmeer (NL); Gary Nelson Garcia Molina, Madison, WI (US); Stefan Pfundtner, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 253 days.

(21) Appl. No.: 15/525,322

(22) PCT Filed: Nov. 11, 2015

(86) PCT No.: PCT/IB2015/058698
§ 371 (c)(1),
(2) Date: May 9, 2017

(87) PCT Pub. No.: WO2016/083929
PCT Pub. Date: Jun. 2, 2016

(65) Prior Publication Data
US 2017/0340854 A1 Nov. 30, 2017

Related U.S. Application Data

(60) Provisional application No. 62/083,995, filed on Nov. 25, 2014.

(51) Int. Cl.
*A61M 21/02* (2006.01)
*A61B 5/0484* (2006.01)
(Continued)

(52) U.S. Cl.
CPC ......... *A61M 21/02* (2013.01); *A61B 5/04845* (2013.01); *A61B 5/4812* (2013.01);
(Continued)

(58) Field of Classification Search
CPC ........ A61M 2230/10; A61M 2230/005; A61M 21/02; A61B 5/4812
See application file for complete search history.

(56) References Cited

U.S. PATENT DOCUMENTS 8,029,431 B2 10/2011 Tononi
2010/0063350 A1 3/2010 Henke et al.
(Continued)

FOREIGN PATENT DOCUMENTS

CN 1187372 A 7/1998
CN 1736327 A 2/2006
(Continued)

OTHER PUBLICATIONS

Callaway III: "Habituation of Averaged Evoked Potentials in Man", Chapter 5 in "Habituation: vol. II. Physiological Substrates"; H.V.S. Peeke and M.J. Hen, Eds. New York: Academic Press, 1973, pp. 153-174.
(Continued)

*Primary Examiner* — Christine H Matthews

(57) ABSTRACT

The present disclosure describes a system configured to adjust the duration of individual sensory stimuli provided to a subject. The system is configured to determine a current amount of slow wave activity in the subject, responsive to the subject being presently in slow wave sleep, control one or more sensory stimulators to provide the individual sensory stimuli to the subject, determine habituation of the subject to the individual sensory stimuli and, responsive to the slow wave activity in the subject for a period of time following the providing of the individual sensory stimuli showing habituation, adjust the duration of the individual sensory stimuli.

15 Claims, 7 Drawing Sheets

(51) Int. Cl.
*A61B 5/00* (2006.01)
*A61M 21/00* (2006.01)

(52) U.S. Cl.
CPC ... *A61B 5/4836* (2013.01); *A61M 2021/0027* (2013.01); *A61M 2205/18* (2013.01); *A61M 2205/3375* (2013.01); *A61M 2205/505* (2013.01); *A61M 2205/52* (2013.01); *A61M 2205/581* (2013.01); *A61M 2205/582* (2013.01); *A61M 2205/583* (2013.01); *A61M 2230/10* (2013.01)

(56) References Cited

U.S. PATENT DOCUMENTS

2012/0277618 A1* 11/2012 Giftakis ............... A61B 5/0022
 600/544

2014/0057232 A1 2/2014 Wetmore et al.

FOREIGN PATENT DOCUMENTS

| JP | 2004089572 A | 3/2004 |
| WO | 2014118650 A1 | 8/2014 |
| WO | 2014118693 A1 | 8/2014 |
| WO | 2014170781 A1 | 10/2014 |

OTHER PUBLICATIONS

Feilding: "Lecture 007 Hearing II"; College of Santa Fe Auditory Theory Lecture Plan, 2014, 12 Page Document.
Totoni et al: "Enhancing Sleep Slow Waves With Natural Stimuli"; Medicamundi, vol. 54, No. 2, 2010, pp. 82-88.
Totoni et al: "Sleep Function and Synaptic Homeostasis"; Sleep Medicine Reviews 92006) vol. 10, pp. 49-62, 2006.

* cited by examiner

SYSTEM AND METHOD FOR ADJUSTING DURATION OF SENSORY STIMULATION DURING SLEEP TO ENHANCE SLOW WAVE ACTIVITY

CROSS-REFERENCE TO PRIOR APPLICATIONS

This application is the U.S. National Phase application under 35 U.S.C. § 371 of International Application No. PCT/IB2015/058698, filed on Nov. 11, 2015, which claims the benefit of U.S. Provisional Patent Application No. 62/083,995, filed on Nov. 25, 2014. These applications are hereby incorporated by reference herein.

BACKGROUND

1. Field

The present disclosure pertains to a system and method for adjusting duration of sensory stimulation during sleep to enhance slow wave activity in a subject.

2. Description of the Related Art

Systems for monitoring sleep are known. Sensory stimulation during sleep is known. Sensory stimulation during sleep is often applied continuously at intervals and/or intensities that do not necessarily correspond to sleeping patterns of a subject. The present disclosure overcomes deficiencies in prior art systems particularly associated with habituation (i.e. decrease in the slow wave activity enhancing effect due to the lack of perceived novelty in the stimulation).

SUMMARY

Accordingly, one or more aspects of the present disclosure relate to a system configured to adjust parameters of individual sensory stimuli provided to a subject. The system comprises a sensory stimulator configured to provide individual sensory stimuli to the subject, one or more sensors configured to generate output signals conveying information related to brain wave activity in the subject during a current sleep session, and one or more physical computer processors. The one or more physical computer processors are configured by computer readable instructions to: determine, based on the output signals, whether the subject is presently in slow wave sleep; responsive to the subject being presently in slow wave sleep, control the sensory stimulator to provide the individual sensory stimuli to the subject, the individual sensory stimuli having a first parameter; detect habituation of the subject to the individual sensory stimuli having the first parameter, habituation being detected based on the output signals for a period of time following the provision of the individual sensory stimuli having the first parameter; and, responsive to detection of habituation of the subject to the individual sensory stimuli having the first parameter, adjust the first parameter.

Yet another aspect of the present disclosure relates to a method configured to adjust parameters of individual sensory stimuli provided to a subject with a parameter determination system. The system comprises a sensory stimulator, one or more sensors, and one or more physical computer processors. The method comprises: generating output signals conveying information related to brain wave activity in the subject during a current sleep session with the one or more sensors; determining, based on the output signals, whether the subject is presently in slow wave sleep with the one or more physical computer processors; responsive to the subject being presently in slow wave sleep, controlling, with the one or more physical computer processors, the sensory stimulator to provide the individual sensory stimuli to the subject, the individual sensory stimuli having a first parameter; detecting, with the one or more physical computer processors, habituation of the subject to the individual sensory stimuli having the first parameter, habituation being detected based on the output signals for a period of time following the provision of the individual sensory stimuli having the first parameter; and, responsive to detection of habituation of the subject to the individual sensory stimuli having the first parameter, adjusting the first parameter with the one or more physical computer processors.

Still another aspect of present disclosure relates to a system configured to adjust parameters of individual sensory stimuli provided to a subject. The system comprises means for providing individual sensory stimuli to the subject; means for generating output signals conveying information related to brain wave activity in the subject during a current sleep session; means for determining, based on output signals, whether the subject is presently in slow wave sleep; means for, responsive to the subject being presently in slow wave sleep, controlling the sensory stimulator to provide the individual sensory stimuli to the subject, the individual sensory stimuli having a first parameter; means for detecting habituation of the subject to the individual sensory stimuli having the first parameter, habituation being detected based on the output signals for a period of time following the provision of the individual sensory stimuli having the first parameter; and means for, responsive to detection of habituation of the subject to the individual sensory stimuli having the first parameter, adjusting the first parameter.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
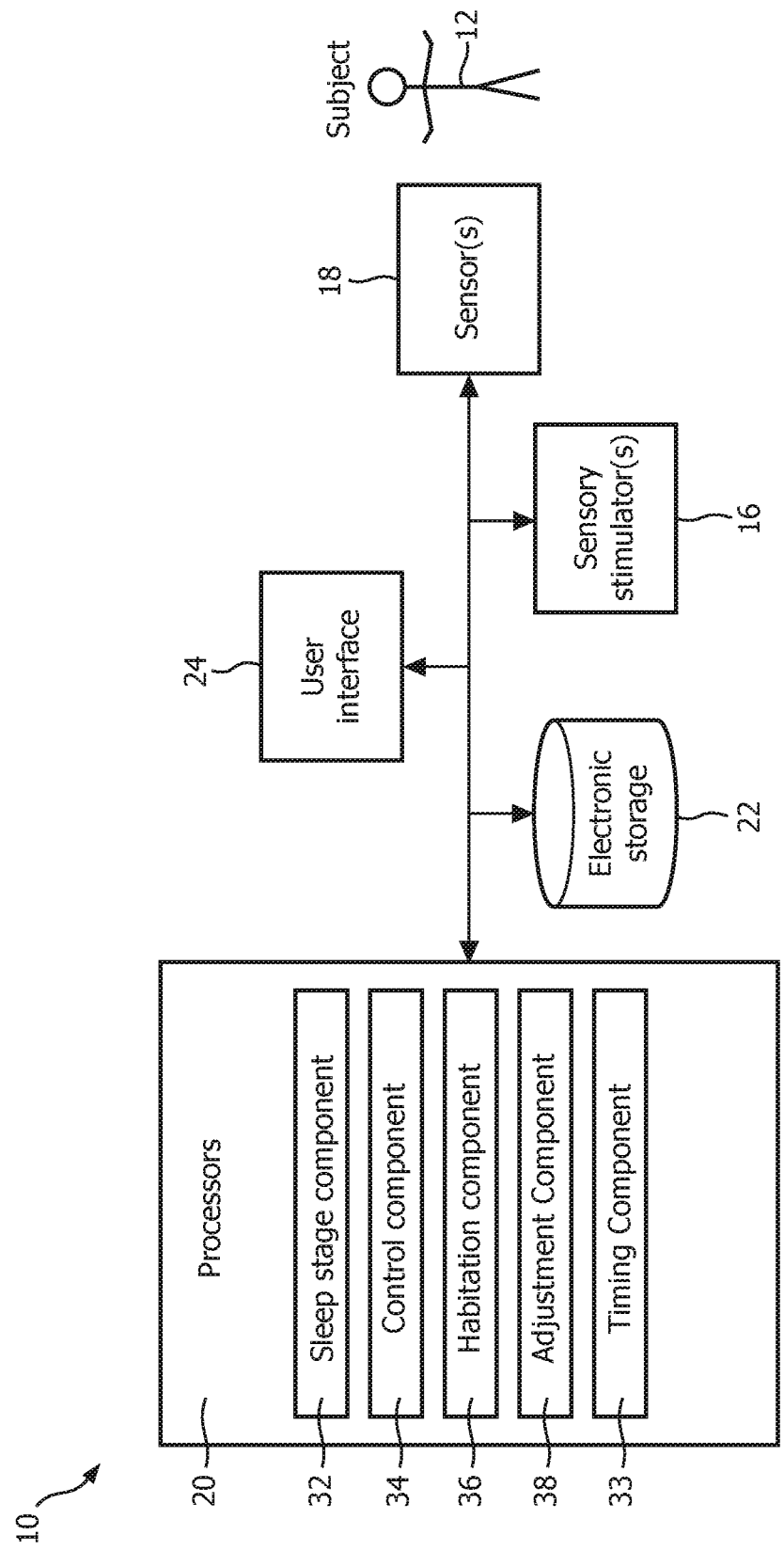
FIG. 1 is a schematic illustration of a system configured to reduce habituation of a subject to sensory stimulation during sleep to enhance slow wave activity during a sleep session of a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates an exemplary embodiment of a system 10 configured to determine and/or adjust parameters (e.g., duration) of a sensory stimulus (e.g., one or more auditory tones) provided to a subject 12 to reduce habituation of subject 12 to the sensory stimuli and increase slow wave activity in subject 12 during a sleep session. In some embodiments, system 10 is configured to determine and/or adjust a duration of individual sensory stimuli provided to a subject 12 to increase sleep slow waves during a sleep session and reduce habituation of subject 12 to the sensory stimulation. Adjusting a duration (e.g. the length of stimulation) of individual sensory stimuli facilitates frequent adjustment of the sensory stimuli to add novelty without being limited by sensitivity (e.g. frequency) and/or safety limitations (e.g. volume). System 10 detects habituation based on the slow wave activity in subject 12. The frequency of sleep slow waves varies from person to person. The frequency of sleep slow waves in a single person may change over time (e.g. with age or depending on sleep-pressure). The frequency of sleep slow waves may change during a single sleep session and/or during a single period of slow wave sleep within a sleep session as subject 12 becomes habituated to sensory stimuli. Sensory stimulation having constant, unchanging parameters may be less effective over time at inducing/enhancing sleep slow waves/slow wave activity due to habituation. System 10 is configured to detect and/or determine an amount of slow wave activity in subject 12 (e.g., immediately following an individual stimulus) and to customize the parameters (e.g., duration) of the sensory stimulation provided to subject 12 to reduce habituation and increase sleep slow waves in subject 12. In some embodiments, system 10 may comprise one or more of a sensory stimulator 16, a sensor 18, a processor 20, electronic storage 22, a user interface 24, and/or other components.

Figure 2:
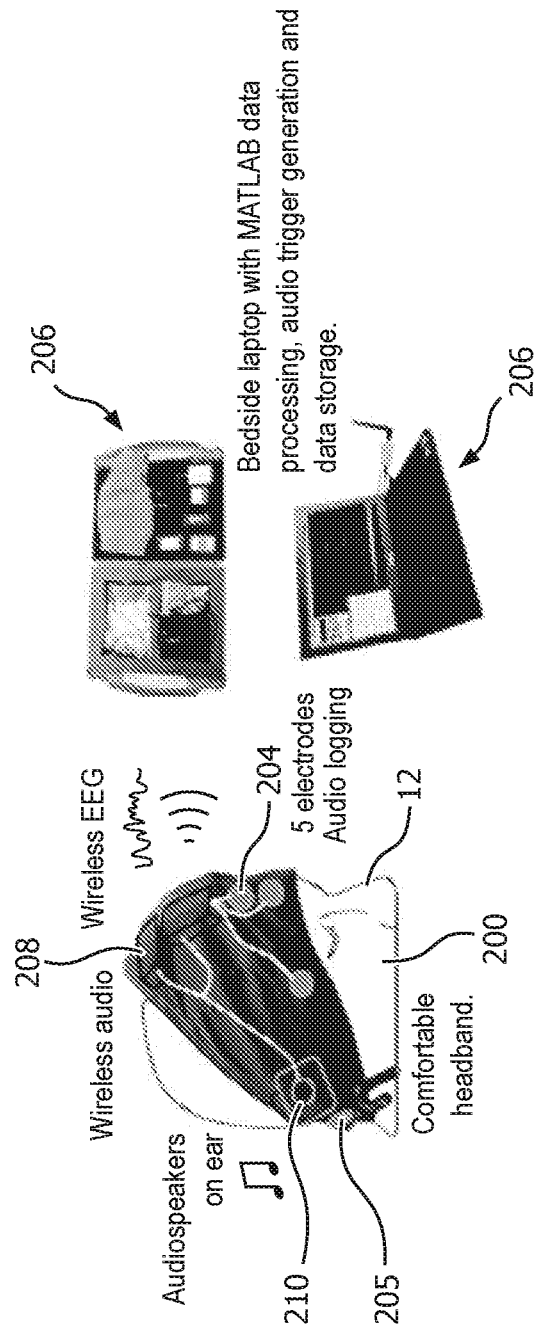
FIG. 2 illustrates an embodiment of the system that includes a subject mount worn by the subject.

In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices. For example, FIG. 2 illustrates a subject mount 200 (e.g., a headband, wristband, and/or other mount) worn by subject 12. Mount 200 includes one or more of sensing electrodes 204, a reference electrode 205, one or more devices 206 associated with an EEG, a wireless audio device 208, one or more audio speakers 210, and/or other components. Audio speakers 210 may be located in and/or near the ears of subject 12. Reference electrode 205 may be located behind the ear of subject 12, for example. In the example shown in FIG. 2, sensing electrodes 204 may be configured to generate output signals conveying information related to the frontal EEG of subject 12, left/right ocular information for subject 12 (e.g. brain wave activity information conveyed in the output signals of sensors 18), and/or other information. The output signals may be transmitted to a computing device (e.g., a bedside laptop included in devices 206) wirelessly and/or via wires. Auditory stimulation may be delivered to subject 12 via wireless audio device 208, speakers 210, and/or other auditory components. An audio signal including information related to auditory stimulation may be generated (e.g., by the computing device included in devices 206). In some embodiments, the audio signal is received by wireless audio device 208. Sensing electrodes 204, reference electrode 205, and devices 206 may be represented, for example, by sensor 18 in FIG. 1. Wireless audio device 208 and speakers 210 may be represented, for example, by sensory stimulator 16 shown in FIG. 1.

Returning to FIG. 1, sensory stimulator 16 is configured to provide sensory stimuli to subject 12. Sensory stimulator 16 is configured to provide sensory stimulation to subject 12 prior to a sleep session, during a sleep session, and/or at other times. For example, sensory stimulator 16 may be configured to provide sensory stimuli to subject 12 during slow wave sleep in a sleep session. Sensory stimulator 16 may be configured to provide sensory stimulation to subject 12 to induce and/or adjust slow wave activity (SWA) in subject 12. In some embodiments, sensory stimulator 16 may be configured such that inducing and/or adjusting SWA includes inducing, increasing, and/or enhancing sleep slow waves in subject 12. SWA corresponds to the power of an electroencephalogram (EEG) signal in the 0.5-4.5 Hz band. In some embodiments, this band is set to 0.5-4 Hz. SWA has a typical behavior throughout cyclic variations of a given sleep session. SWA increases during non-rapid eye movement sleep (NREM), declines before the onset of rapid-eye-movement (REM) sleep, and remains low during REM. SWA in successive NREM episodes progressively decreases from one episode to the next. SWA may be estimated from an EEG for subject 12 during a given sleep session.

In some embodiments, sensory stimulator 16 may be configured to impact (e.g., induce, increase, enhance, and/or otherwise impact) sleep slow waves through non-invasive brain stimulation and/or other methods. Sensory stimulator 16 may be configured to impact sleep slow waves through non-invasive brain stimulation using sensory stimuli. The sensory stimuli include odors, sounds, visual stimulation, touches, tastes, and/or other stimuli. For example, acoustic tones may be provided to subject 12 to induce, increase, and/or enhance sleep slow waves. Examples of sensory stimulator 16 may include one or more of a music player, a tone generator, a collection of electrodes on the scalp of subject 12, a unit to deliver vibratory stimulation (also known as somato-sensory stimulation), a coil generating a magnetic field to directly stimulate the brain's cortex, light generators, a fragrance dispenser, and/or other devices.

Sensor 18 is configured to convey information related to brain wave activity in subject 12 during a current sleep session. In some embodiments, sensor 18 is configured to generate output signals conveying information related to a current sleep stage of subject 12 (e.g., the brain wave activity is related to sleep stage). The current sleep stage of subject 12 may correspond to one or more of non-rapid eye movement (NREM) stage N1, stage N2, or stage N3 sleep, rapid eye movement (REM) sleep, and/or other sleep stages. In some embodiments, NREM stage 3 or stage 2 sleep may be slow wave sleep. Sensor 18 may comprise one or more sensors that measure such information (e.g., brain wave activity/sleep stages) directly. For example, sensor 18 may include electrodes configured to detect electrical activity along the scalp of subject 12 resulting from current flows within the brain of subject 12. Sensor 18 may comprise one or more sensors that generate output signals conveying information related to brain wave activity and/or a current sleep stage of subject 12 indirectly. For example, one or more sensors 18 may generate an output based on a heart rate of subject 12 (e.g., sensor 18 may be a heart rate sensor located on the chest of subject 12, and/or be configured as a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), respiration of subject 12, and/or other characteristics of subject 12. Although sensor 18 is illustrated at a single location near subject 12, this is not intended to be limiting. Sensor 18 may include sensors disposed in a plurality of locations, such as for example, within (or in communication with) sensory stimulator 16, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), and/or in other locations.

Processor 20 is configured to provide information processing capabilities in system 10. As such, processor 20 may comprise one or more of a digital processor, an analog processor, and a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16), or processor 20 may represent processing functionality of a plurality of devices operating in coordination.

As shown in FIG. 1, processor 20 is configured to execute one or more computer program components. The one or more computer program components may comprise one or more of a sleep stage component 32, a slow wave sleep timing component 33, a control component 34, a habituation component 36, an adjustment component 38, and/or other components. Processor 20 may be configured to execute components 32, 33, 34, 36, and/or 38 by software; hardware; firmware; some combination of software, hardware, and/or firmware; and/or other mechanisms for configuring processing capabilities on processor 20.

It should be appreciated that although components 32, 33, 34, 36, and/or 38 are illustrated in FIG. 1 as being co-located within a single processing unit, in embodiments in which processor 20 comprises multiple processing units, one or more of components 32, 33, 34, 36, and/or 38 may be located remotely from the other components. The description of the functionality provided by the different components 32, 33, 34, 36, and/or 38 described below is for illustrative purposes, and is not intended to be limiting, as any of components 32, 33, 34, 36, and/or 38 may provide more or less functionality than is described. For example, one or more of components 32, 33, 34, 36, and/or 38 may be eliminated, and some or all of its functionality may be provided by other components 32, 33, 34, 36, and/or 38. As another example, processor 20 may be configured to execute one or more additional components that may perform some or all of the functionality attributed below to one of components 32, 33, 34, 36, and/or 38.

Sleep stage component 32 is configured to determine whether subject 12 is presently in slow wave sleep based on the output signals from sensor(s) 18 and/or other information. Sleep stage component 32 is configured to determine the current amount of slow wave activity in subject 12 and determine whether the current amount of slow wave activity is indicative of whether subject 12 is presently in slow wave sleep. As described above, the current sleep stage and amount of slow wave activity of subject 12 may correspond to one or more of wakefulness, REM sleep, stage N1, stage N2, and/or stage N3 sleep. Sleep stage component 32 is configured to determine whether subject 12 is presently in slow wave sleep. In some embodiments, slow wave sleep and/or slow wave activity may correspond to stage N3 sleep. In some embodiments, stage N2 and/or stage N3 sleep may be slow wave sleep.

In some embodiments, sleep stage component 32 may determine the current sleep stage of subject 12 based on an analysis of the information conveyed by the output signals of sensor 18. The analysis may include generating and/or monitoring an EEG during the sleep session of subject 12. In some embodiments, the analysis may include detecting slow wave sleep based on a power in a delta band and/or a power in a beta band of the EEG. The power in the delta band is usually defined as the power in the frequency range 0.5-4.5 Hz although there is no standard definition of the frequency limits. The power in the beta band is usually defined as the power in the frequency range 15-30 Hz although variations in limits of the range are very common.

In some embodiments, sleep stage component 32 is configured to determine arousal levels of the subject during the current sleep session. The one or more arousal levels may indicate a level of wakefulness in subject 12. The one or more arousal levels may be determined based on the output signals of sensor(s) 18, information stored in electronic storage 22, testing performed prior to the current sleep session, information received and/or selected via user interface 24, and/or other information. In some embodiments, the one or more arousal levels may be determined based on the analysis of the information related to the EEG. For example, the likelihood for an arousal may be quantified from the EEG power in the beta band in short temporal windows (typically about 1.5 second long, for example). Responsive to the power in the beta band exceeding a threshold, system 10 may detect that an arousal is present. In some embodiments, the beta band power threshold for arousals may be determined based on a previous sleep session of subject 12, based on information related a population of subjects demographically similar to subject 12, and/or based on other information. For example, the beta band power threshold may be determined based on a calibration night of sleep during which the EEG of subject 12 is measured and the statistics of the beta power throughout the sleep session are analyzed to set the threshold. The beta band power threshold may be determined via a database containing the beta thresholds for a population of subjects. The beta band power threshold for subject 12 may be determined based on demographically matching subject 12 with subjects present in the database. Other techniques for determining such a threshold are contemplated.

Slow wave sleep timing component 33 is configured to determine individual time periods of slow wave sleep in subject 12 during the current sleep session. Slow wave sleep timing component 33 is configured to detect the individual time periods of slow wave sleep based on the sleep stage determinations (e.g., whether subject 12 is presently in slow wave sleep) by sleep stage component 32. Slow wave sleep timing component 33 may determine a period beginning point of time, and ending point in time, a length of period, a period midpoint, and/or identifications of a period of time (e.g. indications of slow wave sleep). For example, slow wave sleep timing component 33 may determine a first individual time period of slow wave sleep such that the start of the first individual time period coincides with the start of a first slow wave sleep episode during the current sleep session and/or stops with the end of the first slow wave sleep episode (e.g., sleep stage component 32 determines that subject 12 is no longer in slow wave sleep). The start of a second individual time period of slow wave sleep may coincide with the start of a second episode of slow wave sleep during the current sleep session and/or stops with the end of the second slow wave sleep episode, for example.

In some embodiments, slow wave sleep timing component 33 is configured to determine an amount of time from a period onset of slow wave sleep detected by the sleep stage component 32. In some embodiments, slow wave sleep timing component 33 is configured to determine the individual time periods such that the individual time periods end a predetermined amount of time after sleep stage component 32 determines that subject 12 is presently in slow wave sleep. In some embodiments, the one or more predetermined amounts of time may be based on typical amounts of time between the beginning of slow wave sleep and the end of a slow wave sleep for a given episode of slow wave sleep during the current sleep session. The typical amounts of time may be determined based on a current sleep session of subject 12, previous sleep sessions of subject 12, and/or other sleep sessions. In some embodiments, the one or more predetermined amounts of time may be programmed at manufacture, set by a user via user interface 24, and/or determined by other methods.

In some embodiments, sleep stage component 32 may determine the one or more arousal levels during the individual time periods of slow wave sleep. In some embodiments, slow wave sleep timing component 33 may determine the end of a given individual time period of slow wave sleep based on the arousal levels determined by sleep stage component 32.

Control component 34 is configured to control sensory stimulator 16 to provide the sensory stimuli to subject 12 during the individual time periods of slow wave sleep (e.g., during stage N3 sleep). Control component 34 is configured to control one or more parameters of the sensory stimuli. In some embodiments, control component 34 is configured to control the duration (e.g. the length), the timing, and/or other parameters of the sensory stimuli. Timing and/or duration for delivery of sensory stimulation may correspond to the determination that subject 12 is presently in slow wave sleep, the individual time periods of slow wave sleep, and/or other information. For example, control component 34 is configured such that each individual sensory stimulus may have a specific duration (e.g. a length of stimulation). As another example, control component 34 is configured to control timing of individual stimuli (e.g. a length of time between each individual sensory stimulus). Controlling the duration, timing, and/or other parameters of the individual stimuli may facilitate the introduction of perceived novelty of the stimuli by subject 12 as the stimuli are delivered to subject 12 over time during the sleep session (described further below).

Control component 34 may be configured to control sensory stimulator 16 to provide the sensory stimuli to subject 12 such that the provided sensory stimuli corresponds to sleep stages associated with slow wave activity because the likelihood for slow-wave induction, and/or adjustment during the specific sleep stage may be comparatively higher than in other sleep stages, the user may be less likely to be awakened by the sensory stimuli, and/or for other reasons.

In some embodiments, control component 34 is configured to control sensory stimulator 16 to provide the sensory stimuli in the form of auditory tones that are brief in duration (e.g., about 50 ms long), have a predetermined frequency and/or duration, and are separated from each other by an inter-tone-interval (e.g. timing as described above). In some embodiments, one or more of the auditory tone duration, the frequency, duration, the inter-tone-interval, and/or other characteristics of the sensory stimuli may be programmed at manufacture, set by a user via user interface 24, determined by system 10 based on previous sleep sessions of subject 12, determined based on the current sleep session, and/or determined by other methods. For example, in some embodiments, control component 34 is configured such that the duration is determined based on previous sleep sessions of subject 12, testing performed on subject 12 during wakefulness, and/or other information. The duration may be the shortest duration subject 12 is able to perceive during wakefulness, (e.g. a 200 ms auditory sensory signal), and/or other durations. Information related to the duration of stimulation during previous sleep sessions of subject 12 and/or testing performed on subject 12 during wakefulness may be stored in electronic storage 22, for example. In some embodiments, control component 34 may cause information related to the current sleep session of subject 12 to be stored in electronic storage 22. Information related to the current sleep session may include information related to the duration of the sensory stimulation, the intensity level of the sensory stimulation, sleep stage information, timing information, and/or other information.

Habituation component 36 is configured to detect habituation of subject 12 to the individual sensory stimuli (e.g., stimuli having a first duration controlled by control component 34). Habituation is a decreased response to sensory stimulation (e.g., behavioral and/or cortical). Habituation to a repeated stimulus tends to occur when the stimulus has low novelty as compared to previous stimuli or the environmental context. Habituation is not necessarily due to fatigue of subject 12 but rather a decreased response to the sensory stimuli. Habituation to repetitive sensory stimuli manifests itself as a reduction in amplitude of the cortical response (a decrease in SWA as determined via the EEG and/or other methods). Habituation may adversely affect SWA induction, and/or effectiveness of the sensory stimuli controlled by control component 34. Habituation is detected based on the output signals from sensors 18 for periods of time that follow provision of the individual sensory stimuli, information related to the EEG of subject 12, and/or other information. In some embodiments, habituation component 36 may be thought to determine an effectiveness of the provided sensory stimuli. In some embodiments, habituation component 36 is configured to determine the effectiveness of the provided sensory stimuli based on the measured SWA in subject 12 during a window of time just after the sensory stimulation is delivered to subject 12.

In some embodiments, habituation component 36 is configured to determine whether the individual sensory stimuli having a first duration (200 ms for example) are effective in increasing the slow wave activity of subject 12. In some embodiments, habituation component 36 is configured to determine if two or more consecutive sensory stimuli having the first duration are effective. For example, habituation component 36 may determine there is habituation if the SWA of subject 12 shows decreased effectiveness for two consecutive sensory stimuli. Habituation may be determined by comparing the SWA in a window of time just before the stimulation to the SWA in a window of time just after the stimulation. In some embodiments, habituation is continuously evaluated because the SWA can be instantaneously estimated, by band-pass filtering (preferably in the 0.5-4 Hz band) the EEG, squaring the result, and averaging across a time window (10 second long in some embodiments).

Adjustment component 38 is configured to, responsive to detection of habituation of subject 12 to the individual sensory stimuli (e.g., having a first specific duration parameter), adjust one or more parameters (e.g., duration) of the individual sensory stimuli. Adjustment component 38 is configured to cause control component 34 and/or sensory stimulator 16 to adjust the one or more parameters (e.g. duration, timing, frequency, volume, intensity, etc.) of the provided sensory stimuli. Adjustment component 38 is configured to cause the adjustment based on current parameters (e.g., a current and/or baseline duration) of the sensory stimuli provided to subject 12, information determined by sleep stage component 32, information determined by timing component 33, information determined by habituation component 36, and/or other information. For example, adjustment component 38 may cause the parameter (e.g. duration) of the provided sensory stimuli to be adjusted to a second parameter (e.g. longer or shorter duration) based on whether previously provided stimuli increased SWA in subject 12 and/or habituation to the stimuli was detected by habituation component 36.

In some embodiments, adjustment component 38 is configured such that adjustment includes adjustment based on an adjustment algorithm. The adjustment algorithm may be determined at manufacture, determined based on information entered and/or selected via user interface 24, and/or other information. Algorithm inputs may include information determined by sleep stage component 32, information determined by timing component 33, information determined by habituation component 36, and/or other information. In some embodiments, adjustment algorithm randomly selects the duration of the stimulus (or stimuli sequence) out of a set of durations that is previously predetermined. Adjustment algorithm may leverage the relation between perceived stimulation loudness and tone duration to increase the tone duration when habituation is detected.

In some embodiments, habituation component 36 and/or adjustment component 38 are configured to repeat the habituation and/or effectiveness determination and adjust the parameter one or more times during the individual time periods of slow wave sleep such that the parameter(s) of the sensory stimulation is repeatedly adjusted during the individual time periods of slow wave sleep. Habituation component 36 and/or adjustment component 38 are configured to repeat the habituation and/or effectiveness determination and adjust the parameter of sensory stimuli one or more times until expiration of the individual time periods. For example, habituation component 36 may determine a second habituation and/or effectiveness of the sensory stimuli provided at the second parameter during the first individual time period of slow wave sleep and adjustment component 38 may cause sensory stimulator 16 to adjust the parameter of the provided sensory stimuli to a third parameter of sensory stimuli.

In some embodiments, adjustment component 38 is configured to cause sensory stimulator 16 to adjust the parameter one or more times during a given time period of slow wave sleep until subject 12 is aroused and/or habituation is reduced and effectiveness is restored. In some embodiments, a maximum length of the parameter of sensory stimulus may be determined by adjustment component 38 based on the shortest stimulus that is detected by subject 12 when aroused (e.g. an auditory tone lasting 110 ms). In some embodiments, the maximum parameter may be obtained by adjustment component 38 responsive to user interface 24 receiving entry and/or selection of information related to the maximum parameter. In some embodiments, adjustment component 38 is configured to determine the maximum parameter based on the current sleep session of subject 12 and/or previous sleep sessions of subject 12.

In some embodiments, adjustment component 38 is configured to cause sensory stimulator 16 to cease providing the sensory stimuli to subject 12 during a given period of slow wave sleep responsive to an arousal level determined by sleep stage component 32 breaching an arousal level threshold during the given period of slow wave sleep. In some embodiments, adjustment component 38 is configured to cause sensory stimulator 16 to decrease the intensity of the sensory stimuli provided to subject 12 responsive to the arousal level of the subject breaching the arousal level threshold.

In some embodiments, adjustment component 38 may be configured such that adjustment includes randomly changing one or more parameters (e.g. the duration) of the sensory stimuli (e.g., randomly changing the length of consecutive individual tones provide to subject 12). In some embodiments, randomly adjusting the parameter (e.g. duration) of the sensory stimulation may cause an increase in the arousal level threshold for subject 12. For example, an arousal level threshold determined for auditory stimulation of subject 12 during testing prior to the current sleep session may indicate that subject 12 wakes from sleep responsive to a sound having a duration of 200 ms, for example. Random adjustment of the sensory stimulation may cause subject 12 to wake from sleep at a second lower duration of 190 ms, for example, during the current sleep session.

Figure 3A:
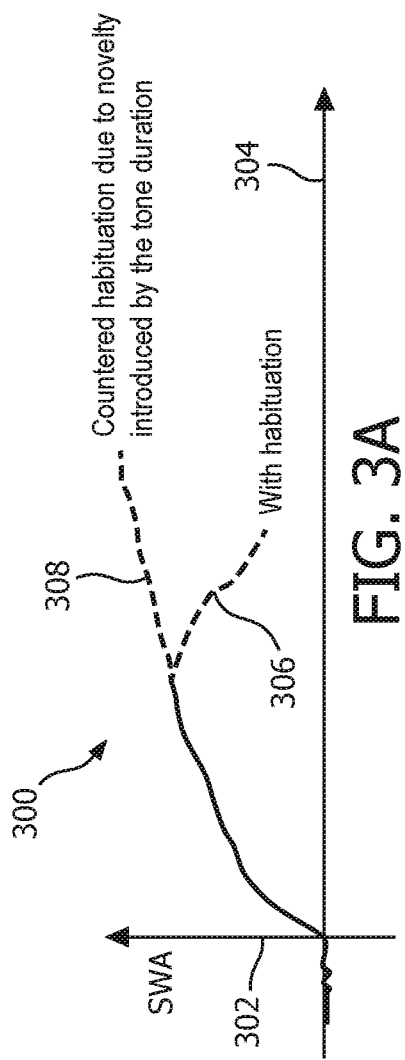
FIG. 3A illustrates the effect of varying a tone duration between blocks of sensory stimulation on the habituation of the subject.

FIG. 3A illustrates a graph 300 showing habituation 306 in subject 12 (FIG. 1). The graph 300 plots Slow Wave Activity (SWA) 302 versus time 304. FIG. 3A shows the enhancement 308 of SWA that can be achieved when habituation 306 is countered with novelty in the sensory stimuli. As described above, novelty may be introduced to a sensory stimulus by adjusting one or more parameters of the stimulus including duration, intensity, frequency, timing, and/or other methods of introducing novelty to the stimulus. In some embodiments, habituation may be detected (e.g., by habituation component 36 shown in FIG. 1) when a slope of the SWA 302 versus time 304 curve turns negative (e.g., by detecting a negative-going zero-crossing).

Figure 3B:
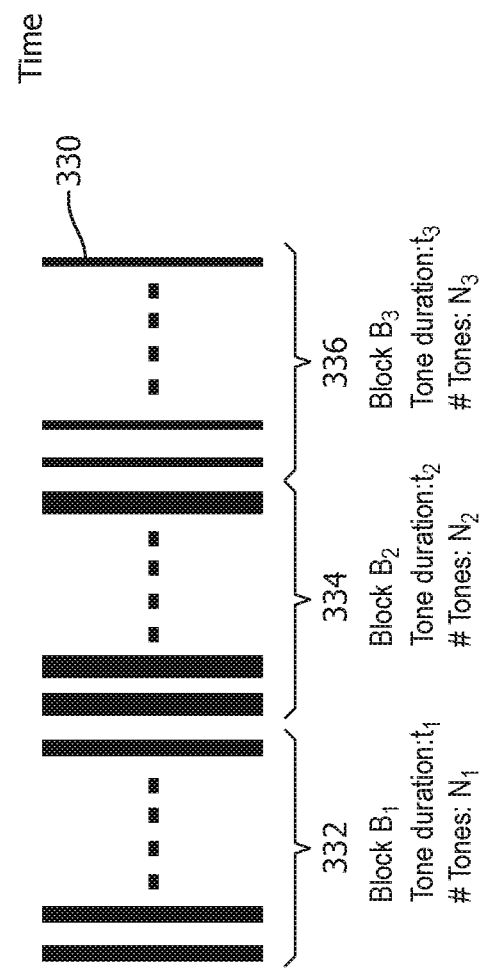
FIG. 3B illustrates grouping individual sensory stimuli to vary timing and duration of the stimuli and introduce novelty.

FIG. 3B illustrates reducing habituation by varying the individual parameters of the sensory stimulation (e.g. tone duration) within and/or by blocks 332, 334, 336 of sensory stimulation. (Control component 34 shown in FIG. 1 and/or other components of system 10 may control sensory stimulator 16 to provide the sensory stimulation in blocks.) Each individual stimulus 330 may have individually adjusted (e.g., by control component 34 and/or adjustment component 36) parameters that introduce novelty and/or the stimuli may be adjusted block by block (e.g., the stimuli in block 332 have a first duration, the stimuli in block 334 have a second duration, and the stimuli in block 336 have a third duration). The blocking of stimuli enables the introduction of novelty through adjusting parameters of the sensory stimulus such as duration and/or timing for individual stimuli, block by block, and/or in other ways.

Figure 4:
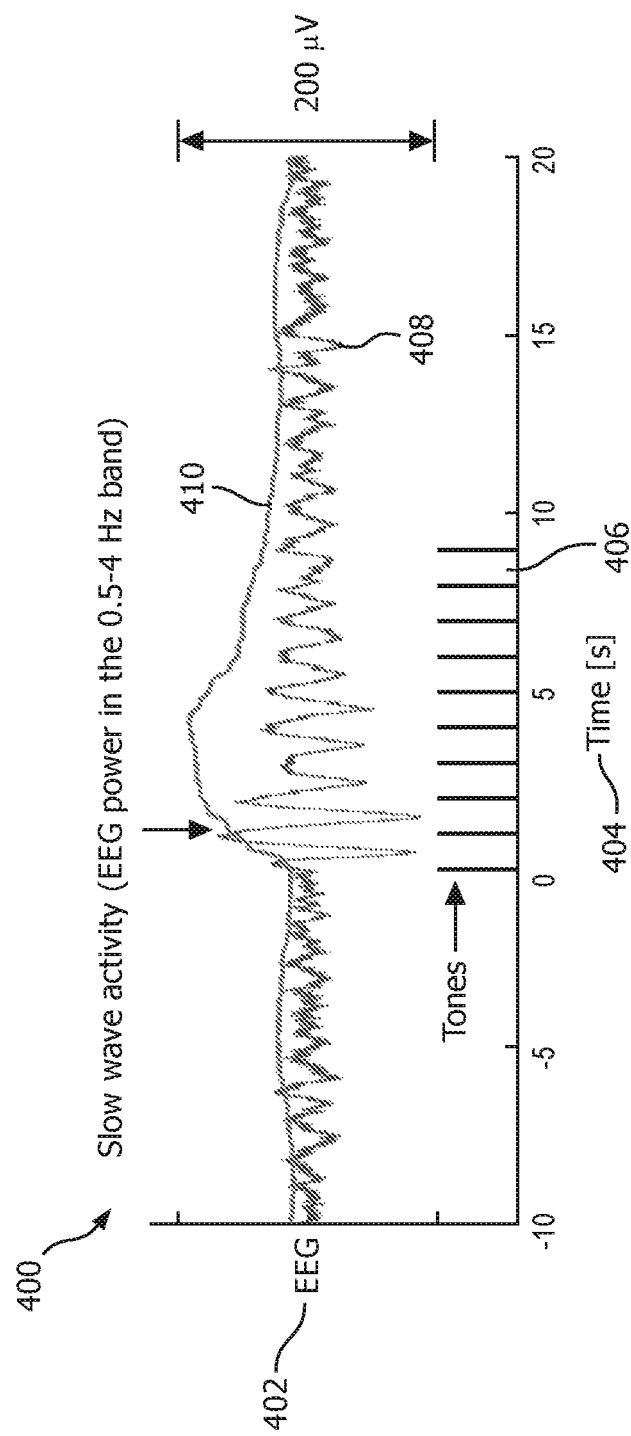
FIG. 4 illustrates the effects on slow-wave activity in response to a sequence of sensory stimulation and the eventual habituation of the subject to the sensory stimulation.

FIG. 4 illustrates the effect of sensory stimuli 406 (e.g. auditory tones) on slow wave activity 410 with EEG data 402 (e.g., EEG power in the 0.5-4 Hz band). A plot 400 of subject 12 (see FIG. 1) shows the EEG frequency 402 versus time 404. When the EEG signal 408 exhibits slow wave sleep, one or more individual sensory stimuli 406 are provided to subject 12. In the example shown in FIG. 4, the sensory stimuli 406 are applied for ten seconds each. As can be seen in plot 400, the slow wave activity 410 after the first several sensory stimuli 406 (e.g., the first 5 sensory stimuli) has a greater response compared to slow wave activity 410 after the last several sensory stimuli 406. The decreased response of slow wave activity 410 to the last several sensory stimuli 406 demonstrates the habituation of subject 12 to the sensory stimuli 406.

Figure 5:
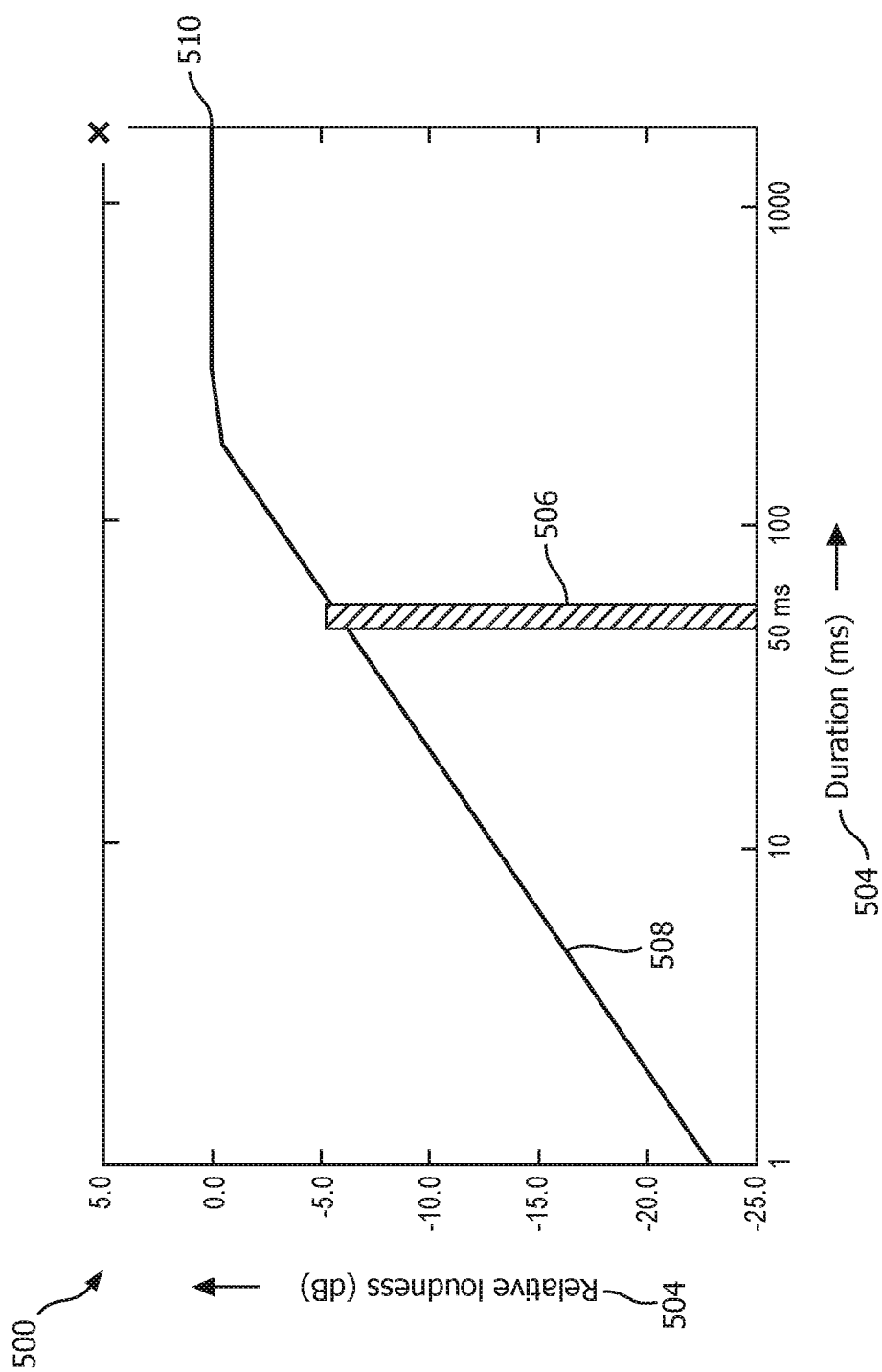
FIG. 5 illustrates the perceived relative loudness of an auditory sensory signal versus tone duration (relative to a 1000 msec stimulus).

FIG. 5 illustrates a perceived relative loudness 502 of an auditory tone (e.g. the same or similar to sensory stimuli 406 shown in FIG. 4) versus tone duration 504. Plot 500 has a log scale for duration 504 and shows that a minor change to the duration 506 may have a large impact on the relative loudness 502 of the perceived auditory sensory signal 508 (this is especially true for short tones, indeed if L is the perceived loudness and D is the duration $\Delta L/\Delta(\log(D))$ =constant→$\Delta L$ is proportional to $\Delta D/D$). Because the human sensory system is less sensitive to 50-millisecond long tones as compared to 200-millisecond or longer tones, duration may enable changes to auditory sensory stimuli without changing tone, pitch, volume, frequency and/or other parameters of the auditory sensory signal. This may enable enhancing novelty of sensory stimuli without having to expose subject 12 to unnecessary mechanical loads and/or volumes. Plot 500 illustrates the sensitivity of the human ear (e.g. approximately 200 ms) where the duration of the auditory sensory signal creates an equisensitive 510 region of relative loudness in the perceived volume experienced by subject 12. From this sensitivity consideration, duration 504 may be a more useful parameter to introduce novelty to subject 12 and reduce habituation. For example, a perceptual increase of ~6 dBs can be obtained if the tone duration increases from 50 to about 200 milliseconds without varying the sound pressure level (e.g. volume). Plot 500 indicates that once the auditory signal duration 506 lasts longer than about 200 milliseconds, the perceived signal is equisensitive 510 in that the perceived auditory signal volume level (e.g. relative loudness 502) does not change. Auditory signal duration 506 can introduce novelty when the duration 504 changes between consecutive tones.

Figure 6:
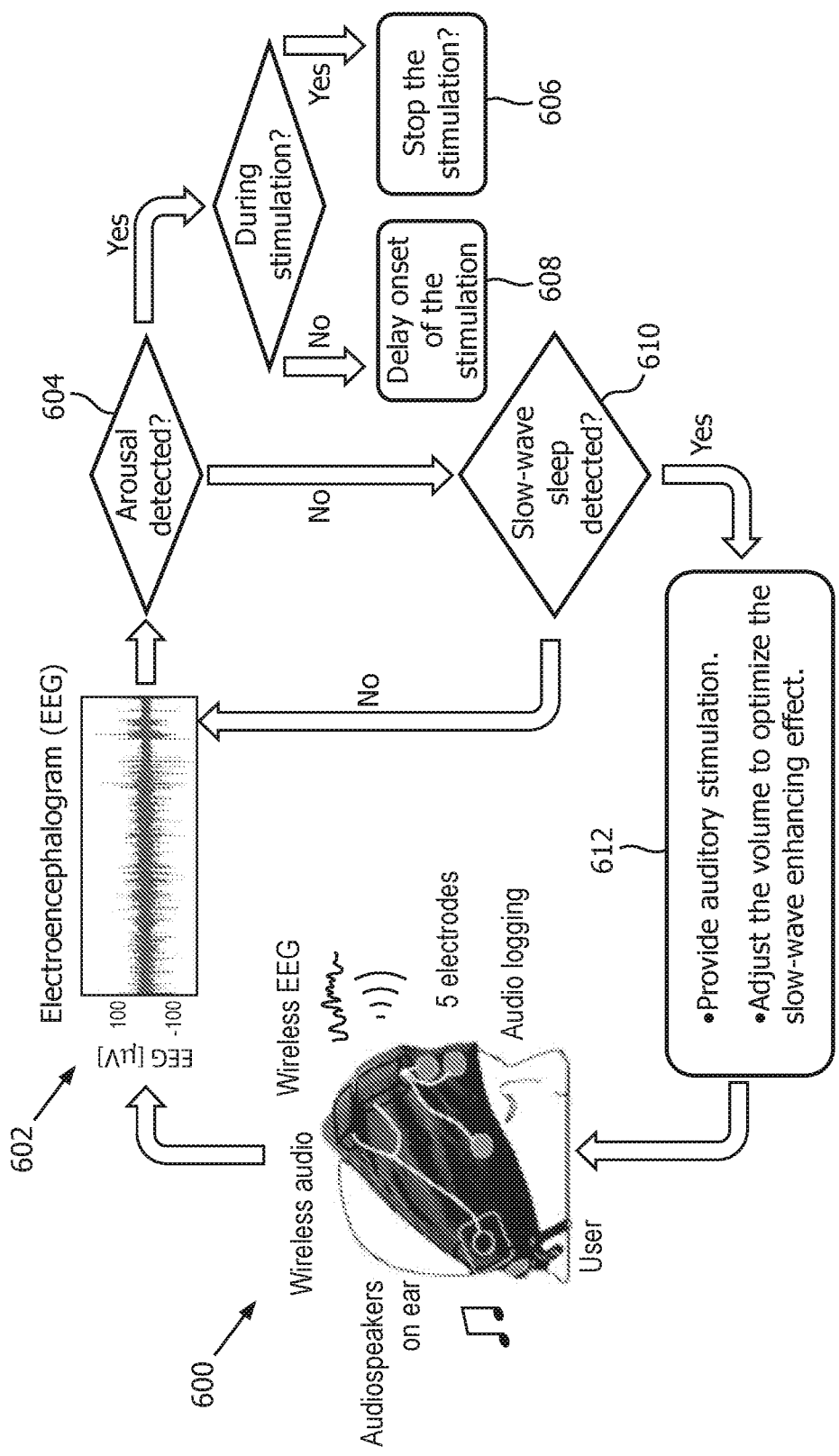
FIG. 6 illustrates one embodiment of the system that detects both arousal and habituation of the subject and adjusts the parameter of the sensory signal based upon the detected arousals and/or habituation.

FIG. 6 illustrates one embodiment of system 10 that detects both arousal and habituation of subject 12 and adjusts parameters of auditory stimulation 612 (e.g. with an adjustment component, the same or similar to adjustment component 38 shown in FIG. 1) based upon EEG signals 602. In the embodiment shown in FIG. 6, a mount 600 (e.g. the same or similar to mount 200 illustrated in FIG. 2) is worn by subject 12. Arousals 604 are events observable in the EEG signal 602 (because of their relatively high frequency content) and indicate that it is likely that subject 12 may be waking up. If an arousal 604 is detected while providing a sensory stimulus 606 (e.g. the same or similar to 406 in FIG. 4) while using system 10, the sensory stimulus immediately stops. If an arousal 604 is detected outside the sensory stimuli duration 608, the onset of the proximate sensory stimulus is delayed. If no arousal 602 is detected, the system detects the occurrence of slow-wave sleep and monitors the sensory stimulus. If slow-wave sleep 610 is detected, then system 10 provides sensory stimulation. In some embodiments the sensory stimulation may consists of a sequence of 50-millisecond long tones spaced from each other by a constant 1-second long interval, for example. One or more parameters of the sensory stimulus (e.g. volume, frequency, and/or duration) of the auditory stimulation may be progressively adjusted to optimize the slow-wave enhancing effect. System 10 can estimate the slow-wave sleep 610 enhancement effect in real-time and can adjust the sensory signal 612 to reduce habituation. As described above, duration of the sensory stimulus may be used to reduce habituation. In some embodiments, one or more parameters may be used in combination to reduce habituation (e.g. increasing volume and adjusting duration).

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received from subject 12, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, an EEG may be displayed to a caregiver via user interface 24.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with sensory stimulator 16 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 7:
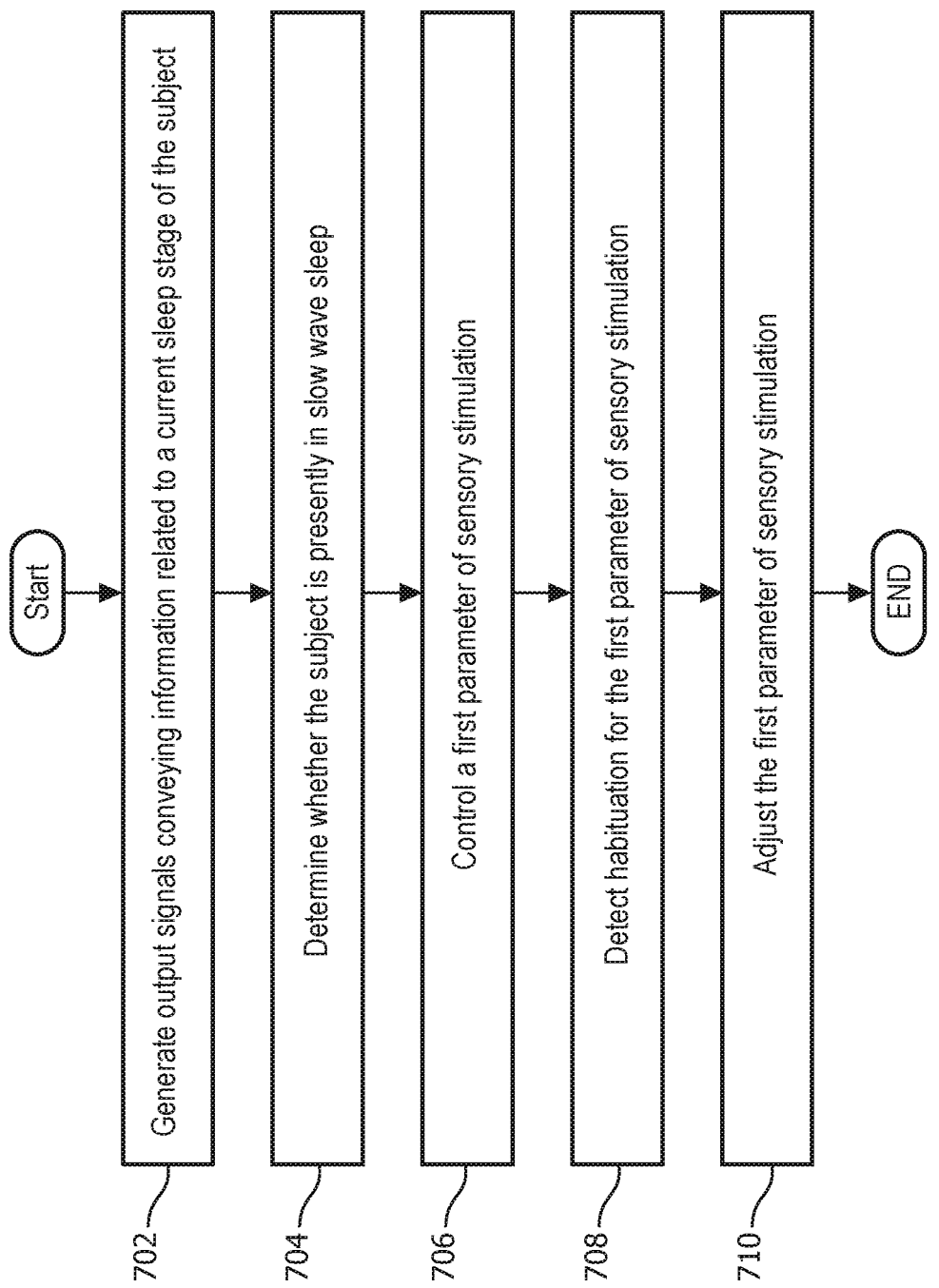
FIG. 7 illustrates a method for adjusting a parameter of sensory stimulation to enhance slow wave activity.

FIG. 7 illustrates a method 700 for adjusting parameters of individual sensory stimuli provided to a subject with a parameter determination system to reduce and/or reduce habituation of the subject to the proved sensory stimuli. The system comprises one or more sensory stimulators, one or more sensors, one or more physical computer processors, and/or other components. The one or more physical computer processors are configured to execute computer program components. The computer program components comprise a slow wave sleep detection component, a probing stimulation component, an identification component, a combination component, a stimulation timing component, and/or other components. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, output signals conveying information related to brain wave activity in the subject during a current sleep session of the subject are generated. In some embodiments, operation 702 is performed by one or more sensors the same as or similar to sensors 18 (shown in FIG. 1 and described herein).

At an operation 704, whether the subject is presently in slow wave sleep is determined, based on the output signals. In some embodiments, operation 704 is performed by a computer program component the same as or similar to sleep stage component 32 (shown in FIG. 1 and described herein).

At an operation 706, responsive to the subject being presently in slow wave sleep, the sensory stimulator is controlled to provide the individual sensory stimuli to the subject. The individual sensory stimuli have a first parameter. The controlling includes controlling the one or more sensory stimulators to provide the first parameter of sensory stimuli. In some embodiments, the first parameter of the sensory stimuli is an intensity level, a timing parameter, a duration, a frequency, and/or other parameter of the individual sensory stimuli. In some embodiments, the first parameter may be determined based on previous sleep sessions of the subject. In some embodiments, operation 706 is performed by a computer program component the same as or similar to control component 34 (shown in FIG. 1 and described herein).

At an operation 708, habituation of the subject to the individual sensory stimuli having the first parameter is detected. Habituation is detected based on the output signals for a period of time following the provision of the individual sensory stimuli having the first parameter. The habituation is related to a decrease in slow wave activity resulting from the first parameter of the sensory stimuli. Habituation is determined based on the output signals. In some embodiments, operation 708 is performed by a computer program component the same as or similar to habituation component 36 (shown in FIG. 1 and described herein).

At an operation 710, responsive to detection of habituation of the subject to the individual sensory stimuli having the first parameter, the first parameter is adjusted. In some embodiments, the first parameter is randomly adjusted and/or includes a prediction of the reduction in habituation that may be obtained via fitting a curve to the sleep slow waves and extrapolating the result to the time instants where the stimulation is delivered. In some embodiments, operation 710 is performed by a computer program component the same as or similar to adjustment component 38 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to adjust parameters of individual sensory stimuli provided to a subject, the system comprising:
   a sensory stimulator configured to provide the individual sensory stimuli to the subject;
   one or more sensors configured to generate output signals conveying information related to brain wave activity in the subject during a current sleep session; and
   one or more physical computer processors configured by computer readable instructions to:
   determine, based on the output signals, whether the subject is presently in slow wave sleep;
   responsive to the subject being presently in slow wave sleep, control the sensory stimulator to provide the individual sensory stimuli to the subject, the individual sensory stimuli having one or more parameters, the one or more parameters including duration of the individual sensory stimuli;
   detect a habituation of the subject to the individual sensory stimuli, the habituation being detected based on the output signals for a period of time following the provision of the individual sensory stimuli; and
   responsive to detection of the habituation of the subject to the individual sensory stimuli, adjust the duration of the individual sensory stimuli such that the adjusting of the duration of the individual sensory stimuli is set to change a perception of an attribute of the individual sensory stimuli without adjusting the attribute, wherein the individual sensory stimuli comprises sound and the attribute comprises volume, and wherein the adjusting of the duration of the sound effectuates a change of perceived volume of the sound.

2. The system of claim 1, wherein the one or more physical computer processors are configured such that the habituation is detected based on a derivative and/or an analysis of a trend of a slow wave activity versus a time curve for the subject.

3. The system of claim 1, wherein the one or more physical computer processors are configured such that adjusting the duration of the individual sensory stimuli includes increasing and/or decreasing the duration of the individual sensory stimuli.

4. The system of claim 1, wherein the one or more physical computer processors are configured to repeat detecting the habituation and adjusting the duration of the individual sensory stimuli one or more times following provision of the individual sensory stimuli during a sleep session of the subject until slow wave sleep in the subject ceases.

5. The system of claim 1, wherein adjusting the duration of sound by about 150 milliseconds effectuates a change of about 6 dBs in the perceived volume of the sound.

6. A method of operation of a parameter determination system, the system comprising a sensory stimulator, one or more sensors, and one or more physical computer processors, the method comprising:
   generating output signals conveying information related to brain wave activity with the one or more sensors;
   determining, based on the output signals, a slow wave sleep with the one or more physical computer processors;
   responsive to the determination, controlling the sensory stimulator, with the one or more physical computer processors, to provide the individual sensory stimuli, the individual sensory stimuli having one or more parameters, the one or more parameters including a duration of the individual sensory stimuli;
   detecting, with the one or more physical computer processors, a state of habituation relative to the individual sensory stimuli, the habituation being detected based on the output signals for a period of time following the provision of the individual sensory stimuli; and
   responsive to the detection, adjusting, with the one or more physical computer processors, the duration of the individual sensory stimuli, such that the adjusting of the duration of the individual sensory stimuli is set to change a perception of an attribute of the individual sensory stimuli without adjusting the attribute, wherein the individual sensory stimuli comprises sound and the attribute comprises volume, and wherein the adjusting of the duration of the sound effectuates a change of perceived volume of the sound.

7. The method of claim 6, further comprising detecting the habituation of the individual sensory stimuli with the one or more physical computer processors based on a derivative of a slow wave activity versus a time curve.

8. The method of claim 6, wherein adjusting the duration of the individual sensory stimuli with the one or more physical computer processors includes increasing and/or decreasing the duration of the individual sensory stimuli.

9. The method of claim 6, wherein detecting the habituation and adjusting the duration of the individual sensory stimuli are repeated one or more times following provision of the individual sensory stimuli.

10. The method of claim 6, wherein adjusting the duration of sound by about 150 milliseconds effectuates a change of about 6 dBs the perceived volume of the sound.

11. A system configured to adjust parameters of individual sensory stimuli provided to a subject, the system comprising:
    means for providing individual sensory stimuli to the subject;
    means for generating output signals conveying information related to brain wave activity in the subject during a current sleep session;
    means for determining, based on the output signals, whether the subject is presently in slow wave sleep;
    means for, responsive to the subject being presently in slow wave sleep, controlling the sensory stimulator to provide the individual sensory stimuli to the subject, the individual sensory stimuli having one or more parameters, the one or more parameters including a duration of the individual sensory stimuli;
    means for detecting a habituation of the subject to the individual sensory stimuli, the habituation being detected based on the output signals for a period of time following the provision of the individual sensory stimuli; and
    means for, responsive to detection of the habituation of the subject to the individual sensory stimuli, adjusting the duration of the individual sensory stimuli, such that the adjusting of the duration of the individual sensory stimuli is set to change a perception of an attribute of the individual sensory stimuli without adjusting the attribute, wherein the individual sensory stimuli comprises sound and the attribute comprises volume, and wherein the adjusting of the duration of the sound effectuates a change of perceived volume of the sound.

12. The system of claim 11, wherein the habituation is detected based on a derivative of a slow wave activity versus a time curve for the subject.

13. The system of claim 11, wherein adjusting the duration of the individual sensory stimuli includes increasing and/or decreasing the duration of the individual sensory stimuli.

14. The system of claim 11, wherein detecting the habituation and adjusting the duration of the individual sensory stimuli are repeated one or more times following provision of the individual sensory stimuli during a sleep session of the subject until slow wave sleep in the subject ceases.

15. The system of claim 11, wherein adjusting the duration of sound by about 150 milliseconds effectuates a change of about 6 dBs in the perceived volume of the sound.

* * * * *